United States Patent [19]
Harrison et al.

[11] Patent Number: 6,086,909
[45] Date of Patent: Jul. 11, 2000

[54] DEVICE AND METHOD FOR TREATMENT OF DYSMENORRHEA

[75] Inventors: Donald C. Harrison; James H. Liu; Wolfgang A. Ritschel, all of Cincinnati, Ohio; Roger A. Stern, Cupertino, Calif.

[73] Assignee: UMD, Inc., Cincinnati, Ohio

[21] Appl. No.: 09/249,963

[22] Filed: Feb. 12, 1999

Related U.S. Application Data

[63] Continuation-in-part of application No. 09/079,897, May 15, 1998.
[60] Provisional application No. 60/049,325, Jun. 11, 1997.

[51] Int. Cl.[7] .............................. A61F 6/06; A61F 13/02; A61F 6/14
[52] U.S. Cl. .................. 424/430; 424/431; 424/432; 424/434; 424/443
[58] Field of Search .................. 424/423, 434, 424/443, 430, 431, 432

[56] References Cited

U.S. PATENT DOCUMENTS

| | | | |
|---|---|---|---|
| 3,852,155 | 12/1974 | Moore | 195/1.8 |
| 4,016,270 | 4/1977 | Pharriss et al | 424/242 |
| 4,073,743 | 2/1978 | Midler, Jr. et al. | 252/309 |
| 4,250,166 | 2/1981 | Mackawa et al. | 424/81 |
| 4,318,405 | 3/1982 | Sneider | 128/263 |
| 4,405,323 | 9/1983 | Auerbach | 604/285 |
| 4,560,549 | 12/1985 | Ritchey | 424/18 |
| 4,615,697 | 10/1986 | Robinson | 604/890 |
| 4,789,667 | 12/1988 | Makino et al. | 514/161 |
| 4,863,725 | 9/1989 | Deckner et al. | 424/81 |
| 4,983,392 | 1/1991 | Robinson | 424/427 |
| 5,026,543 | 6/1991 | Rijke | 424/81 |
| 5,084,277 | 1/1992 | Greco et al. | 424/433 |
| 5,185,146 | 2/1993 | Altenburger | 424/89 |
| 5,192,802 | 3/1993 | Rencher | 514/535 |
| 5,201,326 | 4/1993 | Kubicki et al. | 128/832 |
| 5,246,697 | 9/1993 | Conte et al. | 424/78.03 |
| 5,273,521 | 12/1993 | Peller et al. | 604/13 |
| 5,275,820 | 1/1994 | Change | 424/426 |
| 5,314,915 | 5/1994 | Rencher | 514/535 |
| 5,330,761 | 7/1994 | Baichwal | 424/469 |
| 5,362,498 | 11/1994 | Aiache | 424/435 |
| 5,393,528 | 2/1995 | Staab | 424/436 |
| 5,527,534 | 6/1996 | Myhling | 424/430 |
| 5,540,581 | 7/1996 | Nair et al. | 514/415 |
| 5,788,980 | 8/1998 | Nabahi | 424/430 |

FOREIGN PATENT DOCUMENTS

WO 87/02576  5/1987  WIPO.
WO 89/03207  4/1989  WIPO.

*Primary Examiner*—Carlos A. Azpuru
*Attorney, Agent, or Firm*—Hana Verny

[57] ABSTRACT

Methods, devices, and compositions for treatment of dysmenorrhea comprise an intravaginal drug delivery system containing an appropriate pharmaceutical agent incorporated into a pharmaceutically acceptable carrier whereby the pharmaceutical agent is released into the vagina and absorbed through the vaginal mucosa to provide relief of dysmenorrhea. The drug delivery system can be a tampon device, vaginal ring, pessary, tablet, suppository, vaginal medicated tampon, vaginal sponge, bioadhesive tablet, bioadhesive microparticle, cream, lotion, foam, ointment, paste, solution or gel. The system delivers a higher concentration to the muscle of the uterus, the primary site for the dyskinetic muscle contraction, which is the pathophysiologic cause of dysmenorrhea.

22 Claims, 8 Drawing Sheets

DEVICE AND METHOD FOR TREATMENT OF DYSMENORRHEA

RELATIONSHIP TO COPENDING APPLICATIONS

This application is a continuation-in-part of the U.S. patent application Ser. No. 09/079,897, filed on May 15, 1998 which claims priority from the copending, commonly assigned provisional application Ser. No. 60/049,325, filed Jun. 11, 1997, under 35 U.S.C. §111(b).

FIELD OF THE INVENTION

The present invention concerns devices, methods, and compositions for treating dysmenorrhea by intravaginal administration of therapeutic and/or palliative drugs to the uterus. In particular, the invention concerns a targeted site of delivery of drugs to the uterus using the medicated intrauterine tampon. The device allows delivery of the drug intravaginally in lower concentrations than those needed for systemic treatment and thus provides for lower systemic concentration and fewer side effects.

BACKGROUND OF THE INVENTION

Dysmenorrhea, which may be primary or secondary, is the occurrence of painful uterine cramps during menstruation. In secondary dysmenorrhea, there is a visible pelvic lesion to account for the pain, whereas only a biochemical imbalance is responsible for primary dysmenorrhea. Primary dysmenorrhea affects 50 percent of postpubescent women, and absenteeism among severe dysmenorrheics has been estimated to cost about 600 million lost working hours or over 2 billion dollars annually. Thus, an effective, simple, and safe treatment of primary dysmenorrhea over a period of several days during menstruation will not only enhance the quality of life for sufferers of dysmenorrhea, but will have a positive economic impact.

The pain of dysmenorrhea originates in the uterus. Systemic administration of analgesic drugs generally by the oral route to the patient has not successfully relieved the condition in many women and the administration is frequently limited by side effects. This failure is believed to be the result of a failure to deliver and achieve an effective dosage level of the analgesic to the muscle in the uterus.

SUMMARY OF THE INVENTION

It is therefore an object of the present invention to provide devices, methods and compositions for treating dysmenorrhea by intravaginal delivery of effective doses of drug to the uterus by transvaginal transport to the uterus, that is, into the uterus via lymphatic and venous channels after absorption through the vaginal mucosa.

It is another object of the present invention to provide safe and convenient devices, methods, and compositions which will promote effective localized transvaginal delivery of drugs which are effective to treat dysmenorrhea.

It is still another object of this invention to provide a medicated device, such as a medicated tampon containing a pharmaceutical agent suitable for intravaginal absorption and transvaginal delivery of the pharmaceutical agent to the uterus.

It is another object of this invention to provide pharmaceutically acceptable compositions which will promote effective intravaginal delivery for the purpose of preventing or treating dysmenorrhea.

In one aspect, the present invention provides a method for treating a human female suffering from dysmenorrhea comprising contacting the vaginal epithelium of the female with a pharmaceutical agent selected from the group consisting of nonsteroidal anti-inflammatory drugs, anti-prostaglandins, prostaglandin inhibitors, COX-2 inhibitors, local anesthetics, calcium channel blockers, potassium channel blockers, β-adrenergic agonists, leukotriene blocking agents, smooth muscle inhibitors, vasodilators, and drugs capable of inhibiting dyskinetic muscle contraction. The agent is in combination with a biocompatible excipient acceptable for application of the agent to the vaginal epithelium. The agent is present in the combination in an amount sufficient to attain a therapeutically effective amount of the agent in the uterine muscle of the individual upon intravaginal application of the combination. In the preferred embodiment, the agent is absorbable through the vaginal mucosa and thereby transmitted via venous and lymphatic channels to the uterus.

Non-limiting examples of nonsteroidal anti-inflammatory drugs suitable for use in the method of the invention include Aspirin, Ibuprofen, Indomethacin, Phenylbutazone, Bromfenac, Fenamate, Sulindac, Nabumetone, Ketorolac, and Naproxen. Examples of local anesthetics include Lidocaine, Mepivacaine, Etidocaine, Bupivacaine, 2-Chloroprocaine hydrochloride, Procaine, and Tetracaine hydrochloride. Examples of calcium channel antagonists include Diltiazem, Israpidine, Nimodipine, Felodipine, Verapamil, Nifedipine, Nicardipine, and Bepridil. Examples of potassium channel blockers include Dofetilide, E-4031, Almokalant, Sematilide, Ambasilide, Azimilide, Tedisamil, RP58866, Sotalol, Piroxicam, and Ibutilide. Examples of β-adrenergic agonists include Terbutaline, Salbutamol, Metaproterenol, and Ritodrine. Vasodilators, which are believed to relieve muscle spasm in the uterine muscle, include nitroglycerin, isosorbide dinitrate and isosorbide mononitrate. Examples of COX-2 inhibitors are Celecoxib, Meloxicam and Flosulide.

In another aspect, the method of the invention includes combining the pharmaceutical agent with a drug delivery system for intravaginal delivery of the agent. Examples of the drug delivery system include a tampon device, vaginal ring, pessary, tablet, vaginal suppository, vaginal sponge, bioadhesive tablet, bioadhesive microparticle, cream, lotion, foam, ointment, solution and gel.

In another embodiment, the delivery system can be a controlled release drug delivery system. Non-limiting examples of a suitable biocompatible excipient for applying the agent include a lipophilic carrier or a hydrophilic carrier. An example of a suitable carrier is a lipophilic carrier such as semi-synthetic glycerides of saturated fatty acids. Non-limiting examples of a hydrophilic carrier include polyethylene glycol having an average molecular weight of 6000, polyethylene glycol having an average molecular weight of 1500, polyethylene glycol having an average molecular weight of 400 or mixtures thereof. The biocompatible excipient can also include a muco-adhesive agent such as alginate, pectin, or cellulose derivative. The biocompatible excipient can also include a penetration enhancer such as bile salts, organic solvents, ethoxydiglycol, or interesterified stone oil.

In one embodiment of the invention, the excipient comprises between about 60 to 90% by weight lipophilic carrier, between about 5 to 25% mucoadhesive agent, and between about 5 to 20% penetration enhancer.

In another embodiment of the invention, the excipient comprises between about 60 to 90% by weight hydrophilic carrier, between about 5 to 25% muco-adhesive agent, and between about 5 to 20% penetration enhancer.

In another embodiment of the invention, the drug delivery system comprises a standard fragrance free lotion formulation sold under the trademark JERGENS® lotion.

In another embodiment, the biocompatible excipient can include glycerin, mineral oil, polycarbophil, carbomer 934P, hydrogenated palm oil, glyceride, sodium hydroxide, sorbic acid, and purified water.

In another embodiment of the invention, the drug delivery system can be a vaginal suppository which includes 75% SUPPOCIRE® AS2, 10% hydroxypropyl methylcellulose, and 15% TRANSCUTOL®.

In another aspect, the invention provides a device for delivering an effective amount of a pharmaceutical agent to the uterus for treating a human female suffering from dysmenorrhea. The device is an absorbent vaginal tampon device having a proximal and a distal end. Located at the distal end is a means for delivery of the agent to the epithelium of the vagina. The device also includes a means for preferentially conveying fluid discharged from the uterus near the proximal end to the tampon and thereby preventing contact of the fluid with the agent. The device also has a means for retrieval of the device, such as a string or tape as used in tampons, vaginal rings and diaphragms.

In one embodiment, the invention provides a tampon device for delivering a pharmaceutical agent to the uterus comprising an absorbent vaginal tampon having a proximal end and a distal end. A cup-shaped porous foam portion at the distal end fits around the cervix of the uterus and contains a pharmaceutical agent for delivery to the cervix. The device may also include a nonabsorbing axial tube having a distal opening and extending through the porous foam cup for conducting blood flow to the absorbent material. A retrieval string or tape connected to the tampon device is also included. The absorbent vaginal tampon may contain any of the above-mentioned drugs and be used as a medicated tampon for individual drug or drug combination delivery.

In another embodiment of a tampon device, the distal porous foam cup has a rim which encircles the cervix. The rim has high concentrations of medication and is positioned away from the direct flow of blood which exudes from the cervix during menstruation.

In another embodiment of a tampon device, the distal porous foam cup has a rim which encircles the cervix. The rim has fingers extending into the fornix areas around the cervix and the tips of the fingers have high concentrations of medication and are positioned away from the direct flow of menstrual blood.

In another embodiment of a tampon device, a distal porous foam section is in the shape of a scoop, which only partially encircles the cervix. The porous foam scoop has a nib-like shape which is designed to wedge itself into the posterior fornix. The porous foam scoop is designed to deliver medication to the vaginal wall along the entire length of the porous foam scoop.

In another embodiment, a tampon device is sheathed in a thin, supple, non-porous material such as a plastic film or a coated gauze that surrounds the absorbent tampon material like a skirt and opens like an umbrella when it comes in contact with the vaginal environment. A band of drug, ideally suspended in a wax-like carrier that melts at body temperature, encircles the sheathed tampon. Contact with vaginal fluids or menstrual flow causes the tampon to swell, forcing the skirt to open like an umbrella and to press tightly against the vaginal wall, putting the drug in contact with the vaginal mucosa while effectively preventing the drug from being absorbed into the tampon.

In another embodiment of a tampon device, distal fibers of the tampon which contact the cervix have high concentrations of pharmaceutical agent for delivery of the agent to the cervical tissue.

In another embodiment of a tampon device, the tampon device has an outer tubing having perforations, the outer tubing is concentric around an axial tube. The device has a distal porous foam section which in its dehydrated state is tight around the outer tubing. A bladder is located proximally to the porous foam and filled with liquid pharmaceutical agent. The bladder is connected to the outer tubing. An outer sheath covers the tampon. The sheath has an annular constriction distal to the bladder such that deployment of the tampon through the distal end of the sheath causes the liquid in the bladder to be forced out distally through the perforated outer tubing and into the porous foam.

In another embodiment of a tampon device, the tampon device has an annular delivery composition around the distal end. The composition contacts the vaginal epithelium for delivery of the agent. A non-absorbing axial tube opens distally and extends into the tampon for conducting blood flow to the absorbent material proximal to the porous foam. The annular composition can be a suppository, foam, paste, or gel.

Embodiments of the invention may include tampon devices of a standard length, or may be longer than standard tampons to facilitate locating the tampon device closer to or in contact with the cervix.

In another aspect, the invention provides a pharmaceutically acceptable composition, in dosage unit form, for intravaginal delivery to a human female for the purpose of treating dysmenorrhea. The composition consists essentially of a combination of an effective amount of a pharmaceutical agent selected from the group consisting of non-asteroidal anti-inflammatory drugs, anti-prostaglandins, prostaglandin inhibitors, local anesthetics, calcium channel blockers, potassium channel blockers, β-adrenergic agonists, potassium channel blockers, leukotriene blocking agents, smooth muscle inhibitors, and drugs capable of inhibiting dyskinetic muscle contraction. The agent is combined together with a nontoxic pharmaceutically acceptable carrier. The pharmaceutically acceptable composition can be a vaginal suppository, bioadhesive tablet, bioadhesive microparticle, cream, lotion, foam, ointment, solution or gel.

Non-limiting examples of nonsteroidal anti-inflammatory drugs suitable for use in the composition of the invention include Aspirin, Ibuprofen, Indomethacin, Phenylbutazone, Bromfenac, Fenamate, Sulindac, Nabumetone, Ketorolac, and Naproxen. Examples of local anesthetics include Lidocaine, Mepivacaine, Etidocaine, Bupivacaine, 2-Chloroprocaine hydrochloride, Procaine, and Tetracaine hydrochloride. Examples of COX-2 inhibitors include Celecoxib, Meloxicam and Flosulide. Examples of calcium channel antagonists include Diltaizem, Israpidine, Nimodipine, Felodipine, Verapamil, Nifedipine, Nicardipine, Piroxicam, and Bepridil. Examples of potassium channel blockers include Dofetilide, E-4031, Almokalant, Sematilide Ambasilide, Azimilide, Tedisamil, RP58866, Sotalol, and Ibutilide. Examples of β-adrenergic agonists include Terbutaline, Salbutamol, Metaproterenol, and Ritodrine. Vasodilators include nitroglycerin, isosorbide dinitrate and isosorbide mononitrate.

In one embodiment of the invention, the composition comprises a sustained release gel. In another embodiment, the composition comprises a sustained release suppository.

DETAILED DESCRIPTION OF THE INVENTION

Drug treatments applied to dysmenorrhea are limited due to drug side effects which prevented any attempt to overcome the condition by administration of higher drug levels to the patient through standard routes. The invention concerns a discovery that this problem could be overcome by focusing the delivery of drug therapy directly to the uterus via the vaginal mucosa, as the uterus is the origin of the painful cramping symptoms of the condition. Greatly increased concentrations of therapeutic drugs suitable for treating dysmenorrhea were now obtained by transvaginal delivery through the vaginal mucosa achieved by intravaginal application of the drugs through delivery systems according to this invention.

Additionally, the invention concerns the discovery that a special circulation exists between the vagina and the uterus, which resembles a portal type circulation, allowing for preferential uptake of the drug in the uterus when drugs are administered intra or transvaginally, preferably using suppositories, medicated tampons, vaginal rings, pessary, tablet or any other means for drug delivery suitable for intravaginal or transvaginal administration. As demonstrated in animal studies, a higher uterine bioavailability permits the administration of the drug at a lower dose. This is due to the vaginal uterine portal circulation.

I. Treatment of Dysmenorrhea

A. A Method for Treatment

A method for treatment of dysmenorrhea is based on the concept that the upper vagina and the uterus have specific blood flow characteristics, either by a portal type circulation or by venous and lymphatic channels to permit preferential delivery of pharmacologic agents from the transvaginal delivery mechanism to the uterus. This permits higher concentrations of pharmacologic agents to be delivered to and accumulated in the uterus than can be accomplished by oral administration. This concept has been confirmed in the rabbit model utilizing several drugs. The rabbit is the classic model for studying transvaginal drug delivery and extrapolations to people have generally be applicable.

The most specific demonstration of the concept has been achieved with the drug ketorolac, a nonsteroidal, non-inflammatory drug, as described in Example 4. Studies described in Example 3 demonstrate preferential binding in the uterus for verapamil and indomethacin with transvaginal delivery as compared to intravenous administration.

In general, the method of the invention comprises intravaginal insertion of a device comprising a therapeutic agent for treatment of dysmenorrhea in a pharmaceutically acceptable, non-toxic carrier combined with a suitable delivery device or system which permits the transvaginal delivery of the drug to the uterus through the vaginal mucosa.

The systems and methods of the invention provide several advantages over oral administration of drugs. First, there is an increased concentration of drug delivered to the uterine muscle due to localized vagina to uterus delivery. This provides for higher uterine bioavailability of the drug by transvaginal delivery where compared to oral administration, as exemplarized in Example 4, in studies with ketorolac. Second, there is reduction of first-pass metabolism in the liver by avoiding the gastrointestinal system. Third, the invention provides a continuous drug depot which allows continuous and uninterrupted delivery of drug over a long period of time. Fourth, and very important, is the reduction of side effects due to lower systemic concentration. For example, the well established gastrointestinal side-effects of non-asteroidal anti-inflammatory drugs (NSAIDs) do not arise with transvaginal administration, in the same way as with oral administration, as described herein.

B. Drua Delivery System

The vaginal drug delivery system provides a sustained delivery of the drug to the vaginal epithelium for the treatment of dysmenorrhea. The delivery system can be a solid object delivery system such as a vaginal ring, pessary, tablet or suppository, for example. Alternatively, it can be a paste or gel having a sufficient thickness to maintain prolonged vaginal epithelium contact. Alternatively, it can be a coating on a suppository wall or a sponge or other absorbent material impregnated with a liquid drug containing solution, lotion, or suspension of bioadhesive particles, for example. Any form of drug delivery system which will effectively deliver the treatment agent to the vaginal endothelium is intended to be included within the scope of this invention.

For purposes of simplifying the description of the invention and not by way of limitation, a suppository drug delivery system will be described hereinafter, it being understood that all effective delivery systems are intended to be included within the scope of this invention.

C. Pharmaceutical Agents

Pharmaceutical agent suitable for intravaginal delivery is any drug which may be formulated with a drug delivery system according to the invention.

Pharmaceutical agents for use in the invention are absorbable through the vaginal mucosa into the special circulation system between the vagina and the uterus. The pharmaceutical agent is preferably selected from the group consisting of nonsteroidal anti-inflammatory drugs (NSAIDs), prostaglandin inhibitors, COX-2 inhibitors, local anesthetics, calcium channel blockers, potassium channel blockers, β-adrenergic agonists, leukotriene blocking agents, smooth muscle inhibitors, and drugs capable of inhibiting dyskinetic muscle contraction.

COX-2 inhibitors, such as Celecoxib, Meloxicam and Flosulide are novel anti-inflammatory and analgesic compounds. These compounds effectively inhibit production of COX-2 enzyme which is induced by pro-inflammatory stimuli in migratory cells and inflamed tissue (*Int. J. Tissue Reactions*, 20:3–15 (1998). Because COX-2 is also involved in reproductive processes, selective COX-2 inhibitors will reduce uterine contractions in preterm labor and relieve painful uterine contractions associated with dysmenorrhea by blocking the prostaglandin receptors in the uterus. Additionally, they may reduce the endometrial bleeding.

Preferred NSAIDs include Aspirin, Ibuprofen, Indomethacin, Phenylbutazone, Bromfenac, Sulindac, Nabumetone, Ketorolac, and Naproxen. Preferred local anesthetics include Lidocaine, Mepivacaine, Etidocaine, Bupivacaine, 2-Chloroprocaine hydrochloride, Procaine, and Tetracaine hydrochloride. Preferred calcium channel antagonists include Diltaizem, Israpidine, Nimodipine, Felodipine, Verapamil, Nifedipine, Nicardipine, and Bepridil. Preferred potassium channel blockers include Dofetilide, E-4031, Imokalant, Sematilide, Ambasilide, Azimilide, Ted isamil, RP58866, Sotalol, Piroxicam, and Ibutilide. Preferred β-adrenergic agonists include Terbutaline, Salbutamol, Metaproterenol, and Ritodrine. Vasodilators, which are believed to relieve muscle spasm in the uterine muscle, include nitroglycerin, isosorbide dinitrate and isosorbide mononitrate. COX-2 inhibitors include Celecoxib, Meloxicam and Flosulide.

D. Pharmaceutical Compositions and Formulations

In order to achieve desirable drug release, the active ingredient is incorporated into an excipient (i.e., vehicle or carrier) for which the drug has low affinity. Hence, hydrophilic drugs are incorporated into lipophilic carriers, and lipophilic drugs will be incorporated into hydrophilic carriers.

Preferred lipophilic carriers for use with hydrophilic drugs include semi-synthetic glycerides of saturated fatty acids, particularly from C8 to C18, such as SUPPOCIRE® AS2 (Gattefosse, Westwood, N.J.).

Preferred hydrophilic carriers, for promoting synergistic drug delivery, include polyethylene glycol or mixtures thereof, such as PEG 6000/PEG 1500, or PEG 6000/PEG 1500/PEG 400, or PEG 6000/PEG 400 (Sigma/Aldrich, St. Louis, Mo.).

The system of the invention preferably also comprises a muco-adhesive agent to bring the released drug in solution into prolonged, close contact with the mucosal surface. The muco-adhesive agent is preferably a polymer such as an alginate, pectin, or cellulose derivative. Hydroxypropyl methylcellulose is particularly preferred for use in the present invention.

The system of the invention may also additionally include a penetration enhancer or sorption promoter to enhance permeation of the drug across the uterine mucosal barrier. Preferred sorption promoters include nonionic surface active agents, bile salts, organic solvents, particularly ethoxydiglycol (e.g., TRANSCUTOL® available from Gattefosse), and interesterified stone oil (e.g., LABRAFIL® M 1944CS available from Gattefosse).

Preferred formulations for hydrophilic drugs comprise between about 60–90% by weight lipophilic carrier, between about 5–25% muco-adhesive agent, and between about 5–20% sorption promoter.

In a general method for preparing a formulation including a hydrophilic drug, the lipophilic carrier is melted at 45–50° C. in a heated vessel. The mucoadhesive agent is added to the carrier with stirring. The preferred hydrophilic drug is dissolved in the sorption promoter, and the drug/sorption promoter solution is added to the carrier/muco-adhesive agent solution. The final formulation is poured into molds of the desired size and shape, which are then placed in a refrigerator at 4–6° C.

Preferred formulations for lipophilic drugs comprise between about 50–90% hydrophilic carrier, between about 5–20% muco-adhesive agent, and between about 5–25% sorption promoter.

In a general method for preparing a formulation including a lipophilic drug, the hydrophilic carrier is melted at an appropriate temperature for the particular PEG used in a heated vessel. The muco-adhesive agent is added to the carrier with stirring. The preferred lipophilic drug is dissolved in the sorption promoter, and the drug/sorption promoter solution is added to the carrier/muco-adhesive agent solution. The final formulation is poured into molds of the desired size and shape, which are then placed in a refrigerator at 4–6° C.

The controlled release drug delivery system must be capable of controlled release of a drug into the vagina over several hours or more. During the menstrual cycle, the pH of the vagina changes. Drug delivery systems with buffers to enhance absorption are included in the present invention. The delivery system must be capable of functioning in the presence of menstrual blood and should be easily removable, for example, attached to a string or tape.

Solid phase drug carriers are preferred, because carriers that dissolve or can be diluted out can be carried away by menstrual blood. Advantages of a solid carrier include: 1) no increase in messiness; 2) carrier will not promote bacterial overgrowth with menstrual blood present; 3) carrier may be washable or reusable (e.g., vaginal ring).

E. Devices for Intravaginal Drug Delivery

The controlled release drug delivery system can be in the form of, for example, a tampon-like device, vaginal ring, pessary, tablet, paste, suppository, vaginal sponge, bioadhesive tablet, bioadhesive microparticles, cream, lotion, foam, paste, ointment, or gel. Each of these systems is discussed below.

Figures 1, 2, 3, 4, 5:
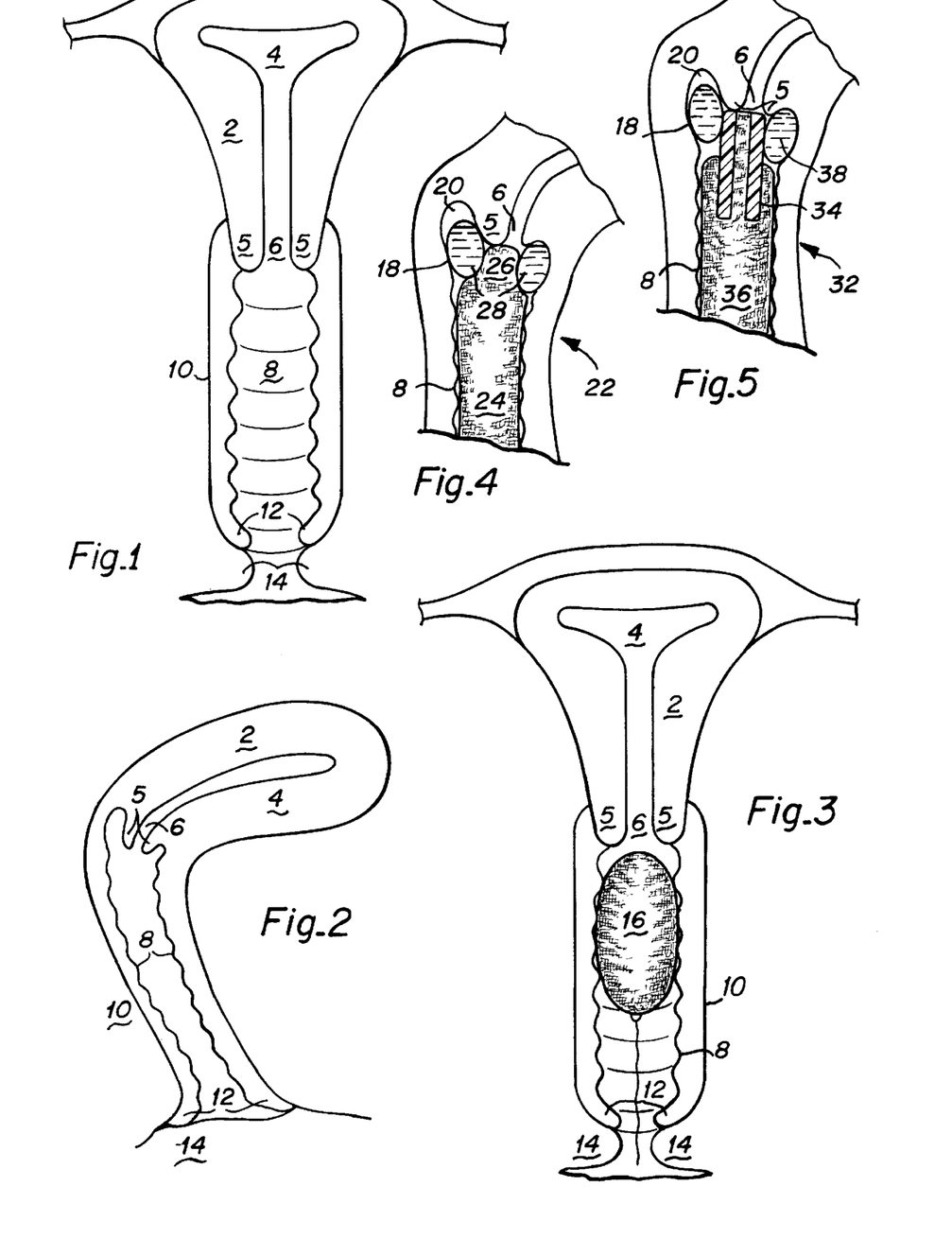
FIG. 1 is a cross-sectional representation of a portion of the female reproductive organs including the uterus and vagina in the upright orientation.
FIG. 2 is a cross-sectional side view representation of a portion of the female reproductive organs including the uterus and vagina.
FIG. 3 is the representation of FIG. 1 showing placement of a vaginal suppository in a first embodiment of a drug delivery system according to the present invention.
FIG. 4 is a cross-sectional side view representation of the vaginal area adjacent the cervix showing placement of a first embodiment of a tampon drug delivery system incorporating an annular delivery composition.
FIG. 5 is the representation of FIG. 2 showing placement of a second embodiment of a tampon drug delivery system according to the present invention.

FIG. 1 is a cross-sectional representation of a portion of the female reproductive organs, including the uterus and the vagina in the upright orientation, and FIG. 2 is a cross-sectional side view representation thereof. The uterus 2 is a muscular organ enclosing the womb 4, and opening at the cervix 5 via the cervical canal or cervical os 6. The vagina 8 is defined by a muscular tube 10 leading from the labia minora 12 and labia majora 14 to the cervix 5. The local vasculature associated with the walls of the vagina 8 communicate with the uterine muscle vascular and lymphatic systems (not illustrated).

FIG. 3 is a cross-sectional representation of FIG. 1 showing placement of a drug delivery system 16 in the vagina 8a position which introduces drugs intravaginally to the uterus 2 by way of the vaginal blood vascular and lymphatic systems. Physiologically, this concept has been documented and confirmed in animal experiments reported herein.

Referring now to FIGS. 4–12, there being depicted various embodiments of tampon-like devices which can be used to deliver drugs for treatment of dysmenorrhea according to the invention. If a tampon-like device is used, there are numerous methods by which a drug can be incorporated into the device. For example, the drug can be incorporated into a gel-like bioadhesive reservoir in the tip of the device. Alternatively, the drug can be in the form of a powdered material positioned at the tip of the tampon. The drug can also be absorbed into fibers at the tip of the tampon, for example, by dissolving the drug in a pharmaceutically acceptable carrier and absorbing the drug solution into the tampon fibers. The drug can also be dissolved in a coating material which is applied to the tip of the tampon. Alternatively, the drug can be incorporated into an insertable suppository which is placed in association with the tip of the tampon.

The tampon-like device can be constructed so as to improve drug delivery. For example, the tampon can be shaped to fit in the area of the posterior fornix and pubic symphysis and constructed so as to open up to have maximum surface area of contact for drug delivery. If the drug is in a reservoir on the surface of the device, the shape of the device should be such that it can maintain the reservoir towards a vaginal mucosal orientation for best predictable drug release characteristics.

The tampon device can also be constructed so as to have a variable absorption profile. For example, the drug area at the tip of the tampon device could be different from that of the more proximal area in order to force the drug to diffuse out into tissue, as opposed to down into the absorbent part of the tampon. Alternatively, there could be a non-absorbing channel around the cervix for the first centimeter or so in order to minimize menstrual flow from washing away the drug composition.

The release of drug from the tampon device should be timed to provide proper uterine concentration of the drug over a typical length of use of a tampon device, usually 1–8 hours.

FIG. 4 is a cross-sectional representation of the vaginal area, adjacent the cervix 5, with a first embodiment of a tampon drug delivery system according to the invention. The tampon device 22 comprises an absorbent cylindrical tampon 24 comprised of fibrous material, for example cotton, having around its distal end 26 an annular delivery composition 28. The tampon device 22 places the annular delivery composition 28, supported around the distal end 26 of the tampon device 22, against the upper epithelium 18 of the vagina 8 and posterior fornix 20 for delivery through the vaginal surfaces in which the annular composition 28 is in contact. The annular composition 28 can be an annular suppository, foam, paste, or gel composed of suitable delivery components. Since dysmenorrhea occurs just before and during menses, the uterine discharge is absorbed by the tampon 24 and is prevented from carrying away the treatment composition.

FIG. 5 is a cross-sectional representation of the vaginal area adjacent the cervix 5 with a second embodiment of a tampon drug delivery system according to the invention. In this embodiment, tampon device 32 includes a non-porous tube 34 which communicates with the cervical os 6 for delivery of the menstrual discharge from the cervical os to an absorbent cylindrical tampon 36 comprised of fibers, for example cotton, for absorbing the discharge. The tube 34 prevents contact of the discharge with an annular drug delivery composition 38.

Figure 6:
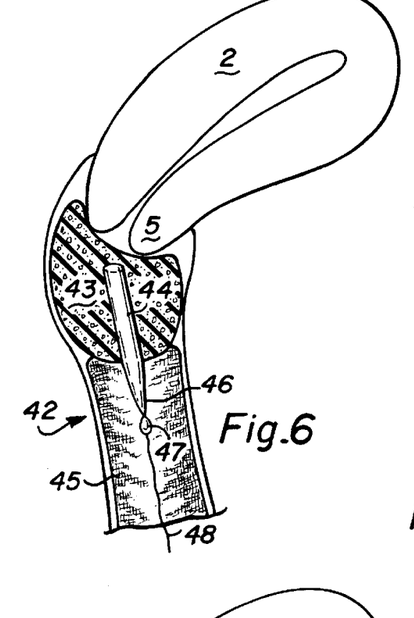
FIG. 6 is the representation of FIG. 2 showing placement of a third embodiment of a tampon drug delivery system incorporating a distal porous foam section.

FIG. 6 is a cross-sectional representation of the vaginal area adjacent the cervix 5 with a third embodiment of a tampon drug delivery system according to the invention. In FIG. 6, the tampon device 42 includes a distal porous foam section 43 which is in the shape of a cup in the expanded state. In the center of the porous foam section 43 is a non-porous tube 44 which will conduct blood flow to absorbent tampon 45 proximal to the porous foam section 43. The porous foam is preferably a soft, light weight, physiologically inert foam material of polyurethane, polyester, polyether, (e.g., as described in U.S. Pat. No. 4,309,997) or other material such as collagen (e.g., as described in U.S. Pat. No. 5,201,326). The axial tube is preferably a non-absorptive physiologically inert material, such as rubber or plastic, and can be coated on its inner surface with an anticoagulant. The proximal end 46 of the tube 44 has a plastic loop 47 to which a string 48 may be tied for removal of the tampon device 42. The cup-shaped porous foam section 43 fits around the cervix 5 of the uterus 2 and contains medication which may be delivered to the cervical tissue.

Figures 7, 7A:
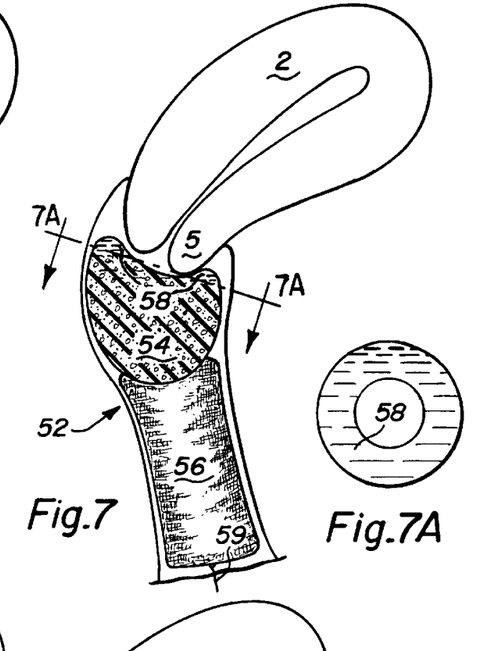
FIG. 7 is the representation of FIG. 2 showing placement of a fourth embodiment of a tampon drug delivery system incorporating a distal porous foam cup.
FIG. 7A is a cross-sectional view of the embodiment shown in FIG. 7, taken in the direction indicated by the arrows labeled 7A in FIG. 7.

FIG. 7 is a cross-sectional representation of the vaginal area adjacent the cervix 5 with a fourth embodiment of a tampon drug delivery system according to the invention. In FIG. 7, the tampon device 52 includes a distal porous foam cup 54 and a proximal absorbent tampon 56. The porous foam cup 54 has a rim 58 which encircles the cervix 5, and which contains high concentrations of medication. The rim 58 area of the porous foam cup 54 is away from the direct flow of blood. The tampon device 52 includes a string 59 for removal of the tampon device 52. FIG. 7A is a cross-sectional view of the embodiment shown in FIG. 7, taken in the direction indicated by the arrows labeled 7A in FIG. 7. As illustrated in FIG. 7A, the rim 58 area forms a ring which contains a high concentration of medication. Alternatively, as illustrated in FIG. 8, the entire porous foam cup 55 may contain medication, not just in the ringed tip area 59 near the cervix 5.

Figures 8, 9, 9A:
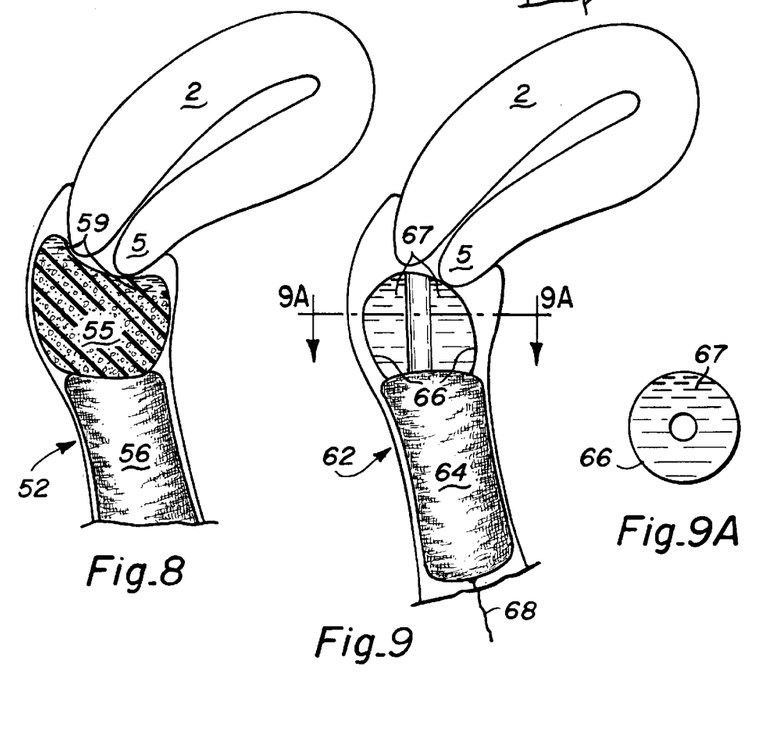
FIG. 8 is an alternate to the embodiment shown in FIG. 7 in which medication is contained in the entire porous foam cup.
FIG. 9 is the representation of FIG. 2 showing placement of a fifth embodiment of a tampon drug delivery system incorporating a distal suppository or gel capsule.
FIG. 9A is a cross-sectional view of the embodiment shown in FIG. 9, taken in the direction indicated by the arrows labeled 9A in FIG. 9.

FIG. 9 is a cross-sectional representation of the vaginal area adjacent the cervix 5 with a fifth embodiment of a tampon drug delivery system according to the invention. In FIG. 9, the tampon device 62 includes a proximal absorbent tampon 64 and a distal section 66 which includes a dissolvable suppository or gel capsule 67 filled with liquid medication. The medication prior to dissolution or release of the liquid has a "doughnut" shape to allow for blood to pass through the center of the tampon 64. The tampon device 62 includes a string 68 attached to the tampon 64 for removal of the tampon device 62. FIG. 9A is a cross-sectional view of the of the embodiment shown in FIG. 9, taken in the direction indicated by the arrows labeled 9A in FIG. 9, and illustrates the doughnut shape of the medication filled suppository or gel capsule 67.

Figures 10, 10A:
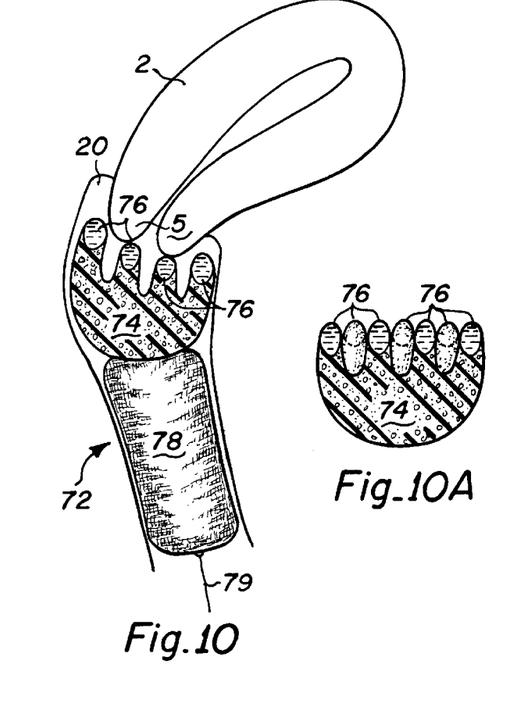
FIG. 10 is the representation of FIG. 2 showing placement of a sixth embodiment of a tampon drug delivery system incorporating a distal foam cup having "fingers."
FIG. 10A is a side view of the distal porous foam cup.

FIG. 10 is a cross-sectional representation of the vaginal area adjacent the cervix 5 with a sixth embodiment of a tampon drug delivery system according to the invention. In FIG. 10, the tampon device 72 includes a porous foam distal section 74 which is in the shape of a cup with "fingers" 76 which extend into the fornix areas 20 around the cervix 5. The tips of the fingers 76 contain high concentrations of medication which may be delivered to areas away from the direct flow of blood as the blood moves into absorbent tampon 78 proximal to the cup-shaped porous foam distal section 74. The tampon device 72 includes a string 79 for removal of the tampon device 72. FIG. 10A is a side view of the porous foam cup 74 and illustrates the fingers 76 which extend into the fornix areas 20 around the cervix 5 (FIG. 10).

It will be readily apparent to a person skilled in the art that the characterization of the drug delivery device as having an annular shape is only an approximate description of the shape formed by fluid or semisolid drug delivery devices positioned around a cylinder and in contact with adjacent vaginal wall epithelium, and all shapes which conform to the vaginal epithelium and external cervical surfaces are intended to be included within and indicated by the term "annular". Moreover, use of the term "annular" does not restrict the invention to the use of such devices which encircle the entire cervix (i.e. 360 degrees). Devices which span an angle of less than 360 degrees, but which make sufficient contact with the vaginal epithelium to deliver sufficient quantity of the drug are within the scope of the invention.

The annular drug delivery composition (FIG. 4 or 5) can be an absorbent material which expands in the presence of fluid or body heat to completely fill the space between the tampon 22, 32 and the vaginal epithelium 18.

Figure 11:
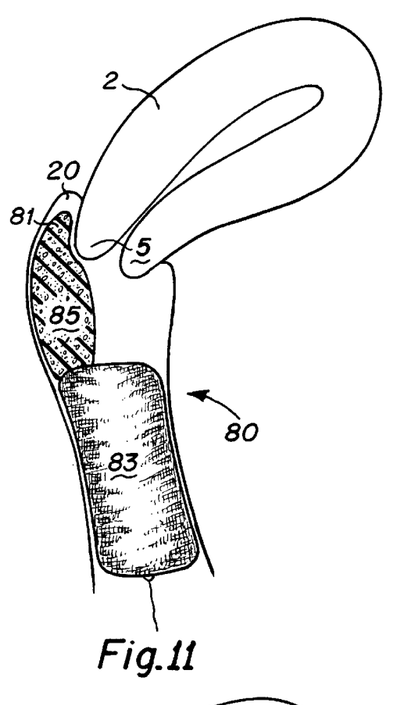
FIG. 11 is the representation of FIG. 2 showing placement of a seventh embodiment of a tampon drug delivery system incorporating a scoop-shaped distal porous foam section.
Figure 12:
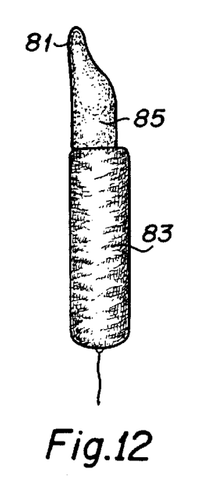
FIG. 12 is a side view of the embodiment shown in FIG. 11.
Figure 13:
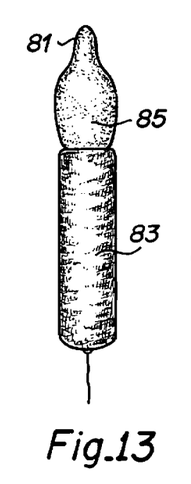
FIG. 13 is a front view of the embodiment shown in FIG. 11.

FIG. 11 illustrates such a drug delivery device having an annular shape which does not completely encircle the entire cervix. FIG. 11 is the representation of FIG. 2 showing placement of a seventh embodiment of a tampon device 80 incorporating a scoop-shaped porous foam section 85. FIG. 12 is a side view of the tampon device 80 and FIG. 13 is a front view of the tampon device 80. The scoop-shaped porous foam section 85 is annular in shape, but does not completely encircle the cervix 5. Instead, the scoop-shaped porous foam section has a nib-shaped tip 81 which is designed to wedge itself into the posterior fornix 20. The scoop-shaped porous foam section 85 is designed to deliver medication to the vaginal wall along the entire length of the scoop-shaped porous foam section 85.

Figure 14:
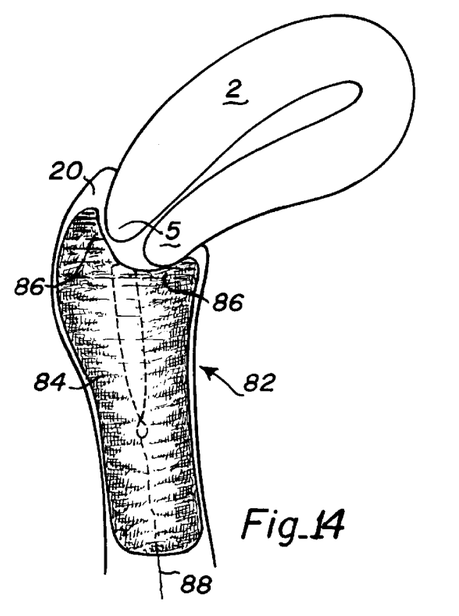
FIG. 14 is the representation of FIG. 2 showing placement of an eighth embodiment of a tampon drug delivery system incorporating distal fibers containing concentrated medication.

FIG. 14 is a cross-sectional representation of the vaginal area adjacent the cervix 5 with an eighth embodiment of a tampon drug delivery system according to the invention. In FIG. 14, the tampon device 82 comprises an absorbent tampon 84. The section 86 of the tampon 84 which rests against the cervix 5 contains high concentrations of medication. As the fibers absorb fluid, the tampon 84 expands around the cervix 5 and delivers medication to the tissue. The blood will be drawn to proximal sections of the tampon 84 as fibers become more absorbent in this area. The tampon device 82 includes a string 88 for removal of the tampon device 82.

Suitable cylindrical cartridge containers or inserter tubes which assist in the insertion and storage of the tampon systems of the present invention will be apparent to those skilled in the art of tampon construction. Examples are described in U.S. Pat. Nos. 4,3178,447; 3,884,233; and 3,902,493.

In general practice, a drug delivery tampon device as described herein is placed into the vagina and the inserter tube is removed. The tampon device contacts the inner wall of the vagina and the penetration enhancer and mucoadhesive act to facilitate the adsorption of the drug into the local vasculature. This results in a higher concentration of the drug being delivered to the uterine muscle where it acts to minimize the pain of dysmenorrhea.

Figures 15, 16, 17:
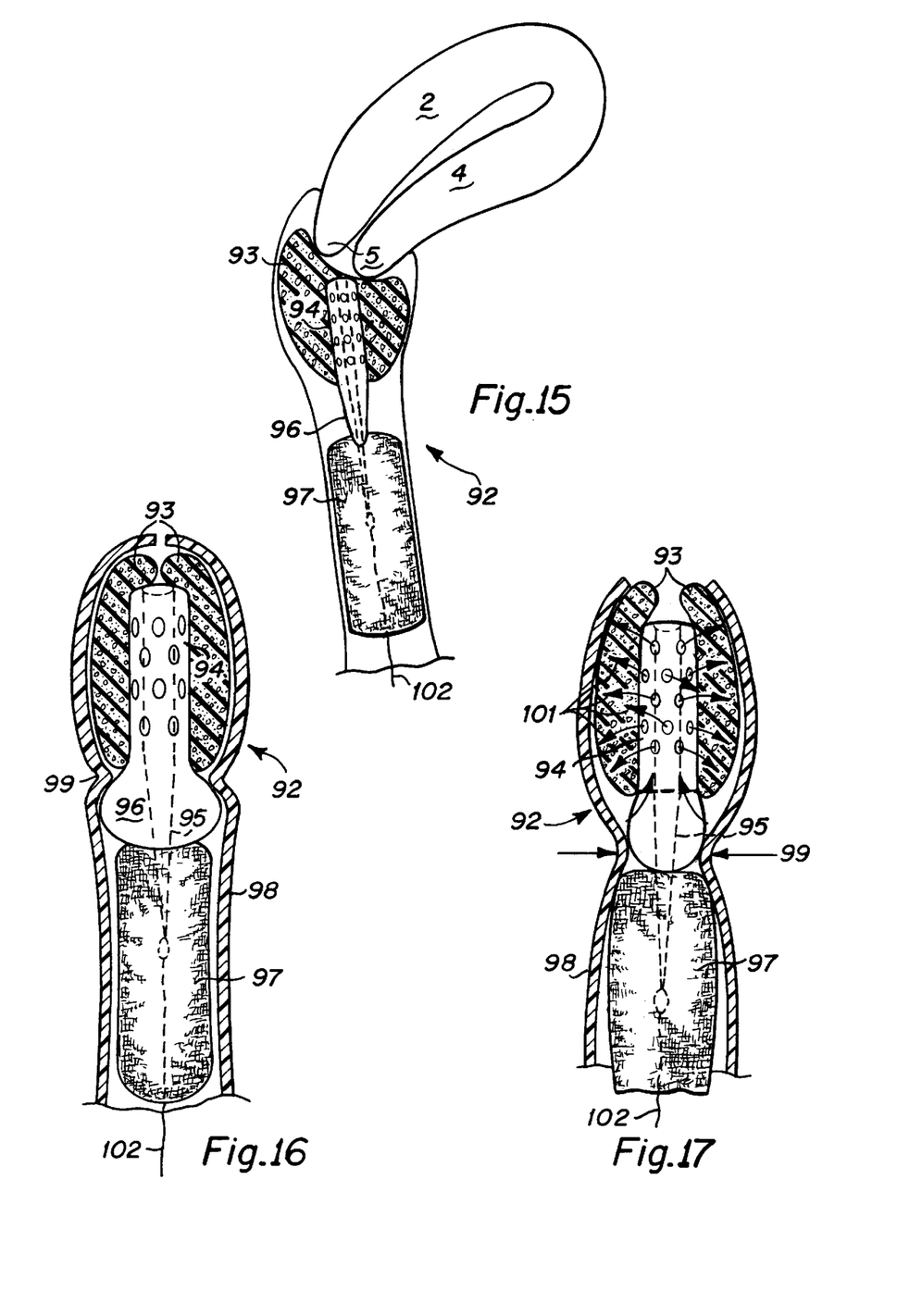
FIG. 15 is the representation of FIG. 2 showing placement of a ninth embodiment of a tampon drug delivery system incorporating non-absorbent tubing having a distal opening.
FIG. 16 is the tampon drug delivery system of FIG. 15 in a dehydrated, sheathed, state.
FIG. 17 is the tampon drug delivery system of FIG. 16 showing deployment of the tampon.

FIG. 15 is a cross-sectional representation of the vaginal area adjacent the cervix 5 with a ninth embodiment of a tampon drug delivery system according to the invention. In FIG. 15, the tampon device 92 includes a distal porous foam section 93 which, in its dehydrated, sheathed state (FIG. 16), is tight around a perforated outer tube 94. The perforated outer tube 94 is connected to a bladder 96 located proximally which is filled with liquid medication (not illustrated). Within the perforated outer tube 94 is a concentric inner tube 95 which provides a pathway for blood to flow into an absorbent tampon 97 which is proximal to the porous foam section 93. Prior to insertion, the tampon device 92 is enveloped in a sheath 98 which is necked down 99 between the porous foam section 93 and the bladder 96 so that, when the tampon device 92 is deployed and the sheath 98 moves over the bladder 96, the medication is forced out 101 through the perforated outer tube 94 into the porous foam section 93 (FIG. 17). The tampon device 92 includes a string 102 for removal of the tampon device 92.

Figure 18A:
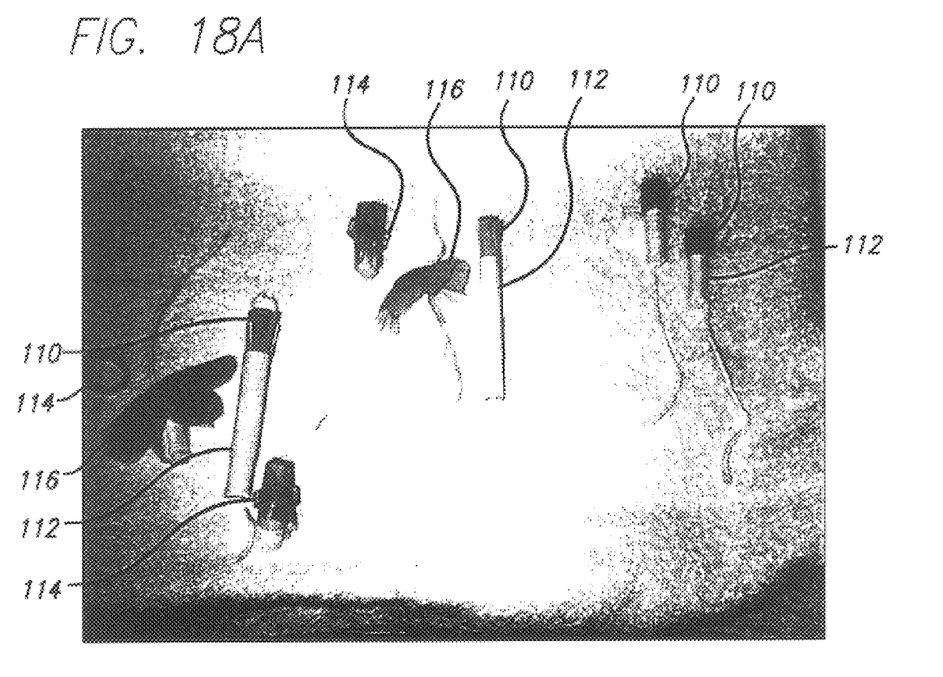
FIGS. 18A and 18B show several configurations of a sheathed tampon of the skirt and umbrella design; with and without medication, both in and out of a cardboard applicator, and in expanded form to simulate device appearance after use.
Figure 18B:
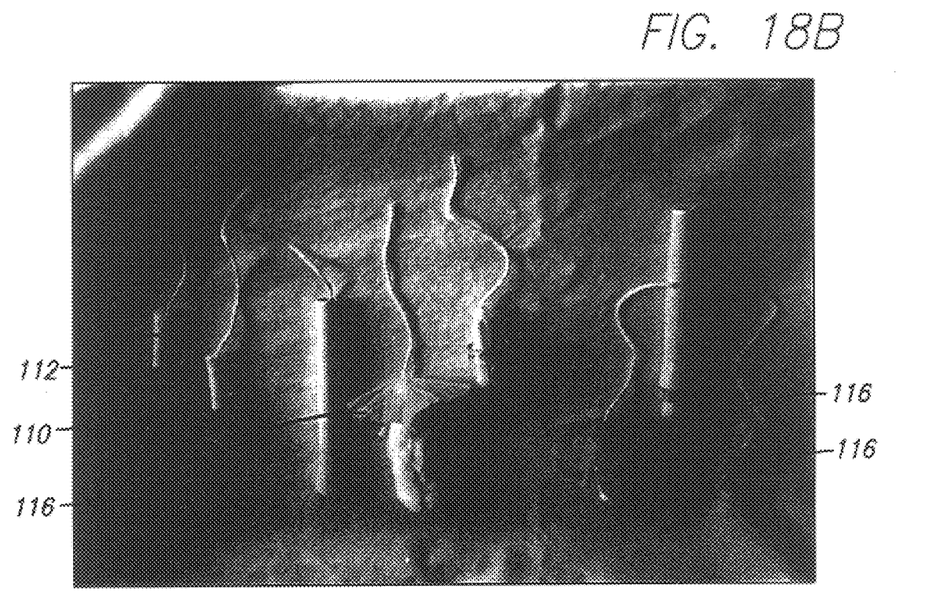

FIG. 18A and 18B show a skirt and umbrella design, wherein the tampon packaged for use is sheathed in a nonporous gauze-like material attached to the proximal end of a tampon in skirt-like fashion (110) with a band of drug in Suppocire, PEG or another carrier configuration encircling the device. Tampon with skirt and medication will fit into a standard cardboard device (112) used for vaginal insertion. When the tampon is inserted into the vagina, the skirt 110 opens up in the umbrella like fashion. The umbrella in opening pushes the medicated surface coverage against the vaginal mucosa and as the tampon absorbs vaginal moisture and menstrual flow it swells to hold the outer surface of the tampon tightly against the mucosal surface. The skirt is typically made of a plastic film similar to cling wraps or bags used in food storage but may be made of any thin, supple nonporous material such as a cloth or gauze, plastic, or cloth or plastic netting material, such as soft organza, tulle or cotton including those that are nonporous due to a coating. Any other suitable material may be used as the skirt material.

Figure 19:
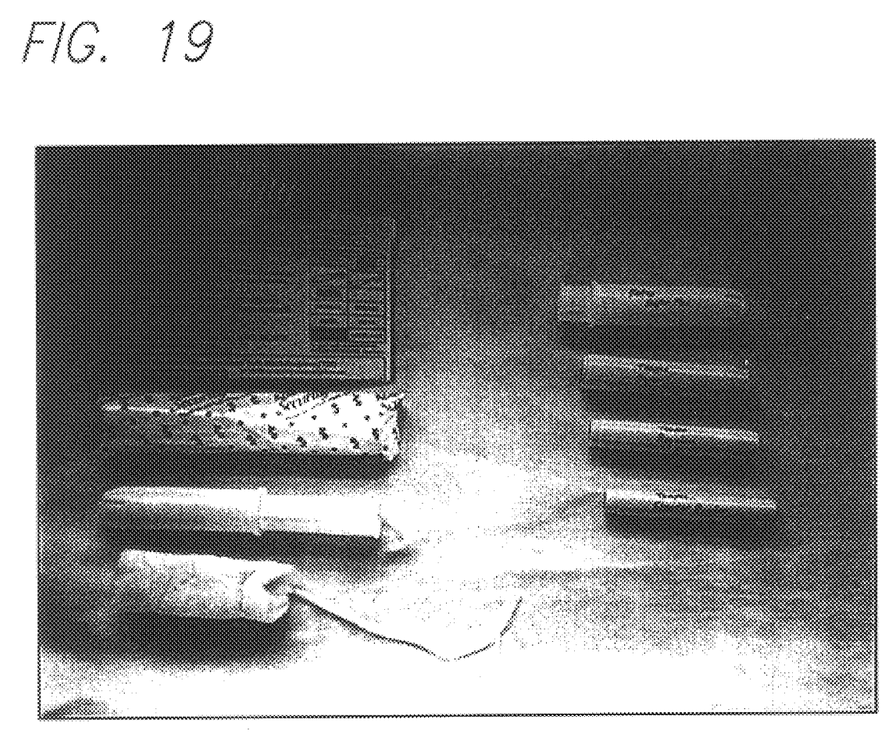
FIG. 19 illustrates the different sizes and styles of tampon inserters currently on the market, the cardboard tube inserters on the right are most appropriate for the FIG. 18 design.
Figure 20A:
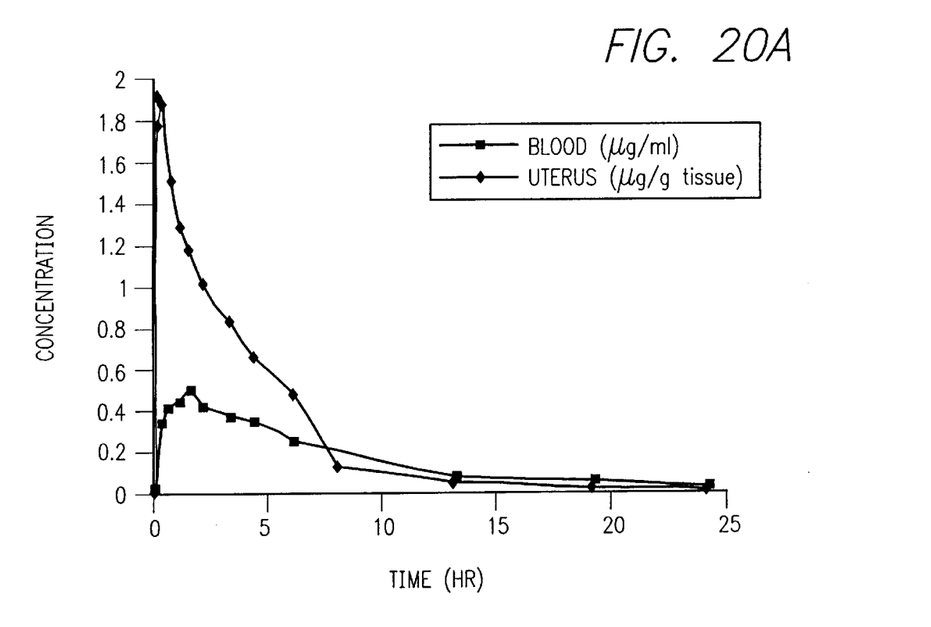
FIG. 20 illustrates concentrations of ketorolac in rabbit blood and uterus ($\mu$/ml) following oral administration (FIGS. 20A and 20B) and vaginal administration (FIGS. 20C and 20D).
Figure 20B:
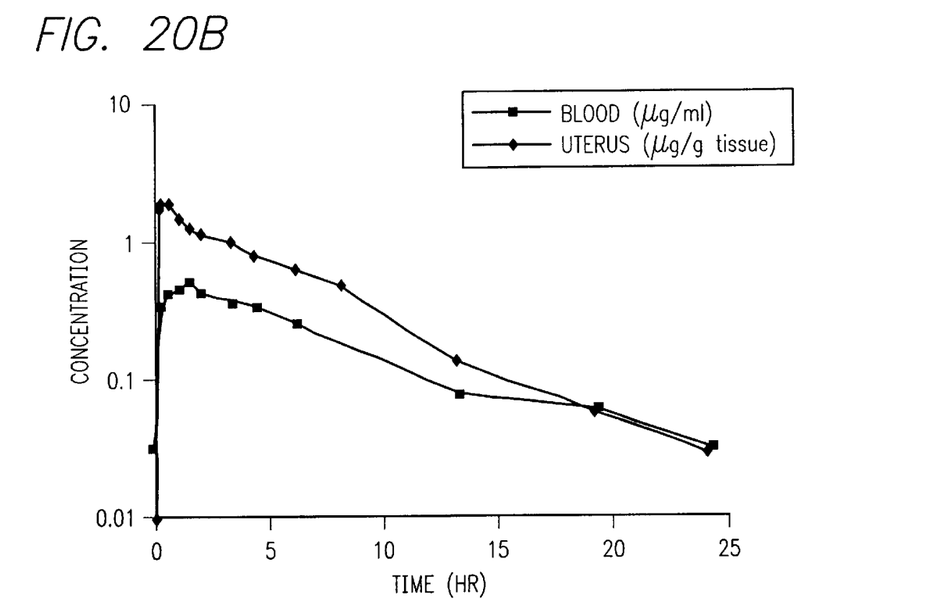
Figure 20C:
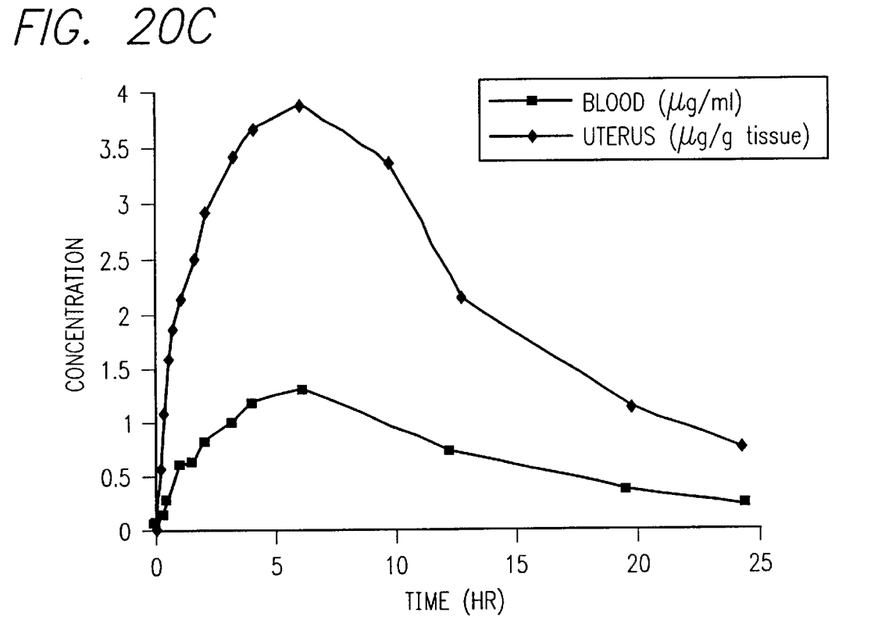
Figure 20D:
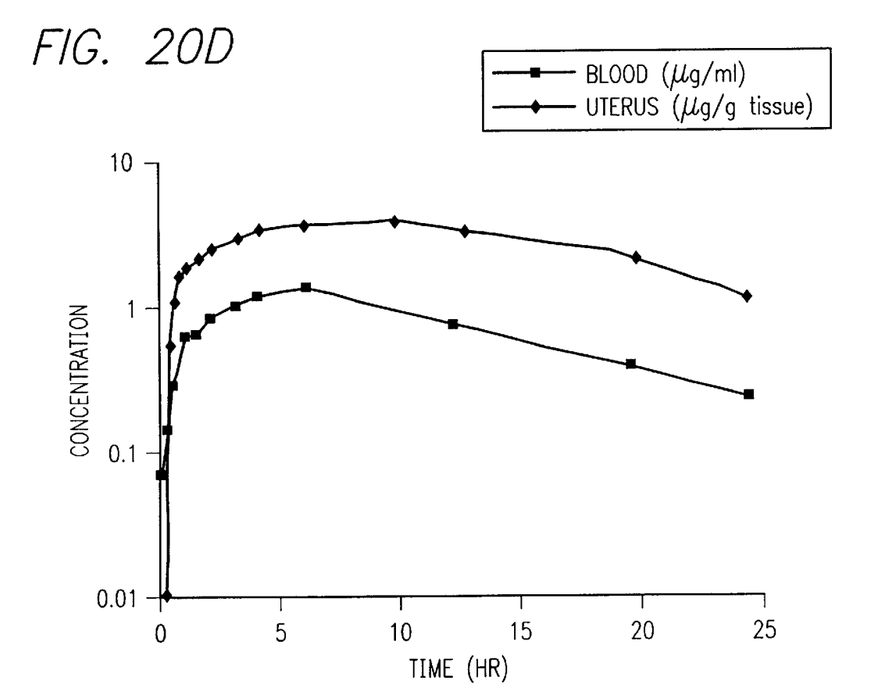

FIG. 19 shows a typical plastic inserter design (left) with a tapered tip, which is not readily useable for the sheathed tampon device. The cardboard inserters on the right have a wide, open tip that is not likely to dislodge the sheath and medication. Cardboard applicators are available in a variety of sizes, making adaptation of current tampon configurations easily accomplished.

Another example of a suitable controlled release drug delivery system for the present invention is the vaginal ring.

Vaginal rings usually consist of an inert elastomer ring coated by another layer of elastomer containing the drug to be delivered. The rings can be easily inserted, left in place for the desired period of time (e.g., up to 7 days), then removed by the user. The ring can optionally include a third, outer, rate-controlling elastomer layer which contains no drug. Optionally, the third ring can contain a second drug for a dual release ring. The drug can be incorporated into polyethylene glycol throughout the silicone elastomer ring to act as a reservoir for drug to be delivered.

Pessaries, tablets and suppositories are other examples of drug delivery systems which can be used in the present invention. These systems have been used for delivery of vaginal medications and steroids, and have been described extensively in the literature.

Another example of a delivery system is the vaginal sponge. The desired pharmaceutical agent can be incorporated into a silicone matrix which is coated onto a cylindrical drug-free polyurethane vaginal sponge, as described in the literature.

Bioadhesive tablets are another drug delivery system. These bioadhesive systems use hydroxy propyl cellulose and polyacrylic acid. They release drugs for up to five days once they are placed in the appropriate formulation.

Bioadhesive microparticles constitute still another drug delivery system suitable for use in the present invention. This system is a multi-phase liquid or semi-solid preparation which does not seep from the vagina as do most current suppository formulations. The substances cling to the wall of the vagina and release the drug over a several hour period of time. Many of these systems were designed for nasal use but can be used in the vagina as well (e.g. U.S. Pat. No. 4,756,907). The system may comprise microspheres with an active drug and a surfactant for enhancing uptake of the drug. The microparticles have a diameter of 10–100 pm and can be prepared from starch, gelatin, albumin, collagen, or dextran.

The drug can also be incorporated into creams, lotions, foams, paste, ointments, and gels which can be applied to the vagina using an applicator. Processes for preparing pharmaceuticals in cream, lotion, foam, paste, ointment and gel formats were discussed above and can be found throughout the literature. An example of a suitable system is a standard fragrance free lotion formulation containing glycerol, ceramides, mineral oil, petrolatum, parabens, fragrance and water such as the product sold under the trademark JERGENS® (Andrew Jergens Co., Cincinnati, Ohio). This formulation was used by Hargrove et al. (Abstract No. 97.051, North American Menopause Society, Boston, Mass., September, 1997) for transcutaneous delivery of estradiol and progesterone. Suitable nontoxic pharmaceutically acceptable systems for use in the compositions of the present invention will be apparent to those skilled in the art of pharmaceutical formulations and examples are described in REMINGTON'S Pharmaceutical Sciences, 19th Edition, A. R. Gennaro, ed., 1995. The choice of suitable carriers will depend on the exact nature of the particular vaginal dosage form desired, e.g., whether the active ingredient(s) is/are to be formulated into a cream, lotion, foam, ointment, paste, solution, or gel, as well as on the identity of the active ingredient(s).

In practice, the drug delivery systems of the invention are applied several hours before or just after onset of menstruation in order to treat or prevent dysmenorrhea. The treatment would continue for a few hours up to 2 to 3 days, as needed, to alleviate and prevent painful menstruation and symptoms such as nausea, fatigue, diarrhea, lower backache, and headache.

Other features of the invention will become apparent in the course of the following descriptions of exemplary embodiments which are given for illustration of the invention and are not intended to be limiting thereof.

All references, patents and patent applications cited herein are hereby incorporated by reference in their entirety.

Procedures described in the past tense in the examples below have been carried out in the laboratory. Procedures described in the present tense have not been carried out in the laboratory, and are constructively reduced to practice with the filing of this application.

EXAMPLE 1

Preparation of Verapamil Vaainal Suppository

The dose of Verapamil (Sigma/Aldrich, St. Louis, Mo.) was 0.15–0.6 mg/kg body weight. Radioactively labeled Verapamil (4–7 $\mu$Ci) $^3$H was added to the unlabeled compound. Vaginal suppositories were formulated and prepared 24 hours prior to each experiment. The three basic ingredients for the suppositories were SUPPOCIRE® AS2 (Gattefosse, Westwood, N.J.) (75% wt); hydroxypropyl methylcellulose (e.g. METHOCEL® K, HPMC K15M) (Dow Chemical, Midland, Mich.) (10% wt), a mucoadhesive agent; and TRANSCUTOL® (Gattefosse) (15% wt). To make eight suppositories, 4.5 grams of SUPPOCIRE, 600 mg of HPMC, 900 mg of TRANSCUTOL, the calculated dose of the drug, and its labeled counterpart were weighed out. SUPPOCIRE was melted in a disposable 100 mL polypropylene beaker suspended in water at 50° C. The solution was stirred until completely melted. HPMC and TRANSCUTOL were then added and mixed. Finally, the unlabeled drug and the radioactively-labeled drug were added to the warm solution. The warm mixture was quickly poured into TYGON® tubing (available from Fisher Scientific, Pittsburgh, Pa) molds (2 cm lengths), the tubing was kept upright on an ice-cold glass slab. Suppositories were kept refrigerated until use. The suppository was weighed prior to each experiment to determine the actual drug dose.

EXAMPLE 2

Preparation of Indomethacin Vaginal Suppository $^{14}$C-Indomethacin was obtained from Amersham Life Science, Arlington Hts., Ill. The dose of cold Indomethacin (Sigma/Aldrich) was 0.2 mg/kg body weight. Labeled Indomethacin (4–7 $\mu$Ci) was added to the cold compound. All of the other steps in the preparation of the Indomethacin suppository are identical to those of Example 1 with Indomethacin replacing Verapamil.

EXAMPLE 3

Verapamil Pharmacokinetic Studies $^3$H-Verapamil was obtained from DuPont/NEN, Boston, Mass. Prior to intravenous injection, cold Verapamil (Sigma/Aldrich, St. Louis, Mo.) (0.15–0.6 mg/kg body weight, i.v.) was dissolved in 0.5 mL dimethyl sulfoxide (Syntex, West Des Moines, Iowa). Labeled Verapamil (4–7 $\mu$Ci) was then added to the cold compound just prior to i.v. injection.

Female white New Zealand rabbits weighing 2.8 to 3.5 kg were obtained from Myrtle Rabbitry (Thompson Station, Tenn.). Rabbits were kept in a National Institutes of Health approved facility and were acclimated to their environment at least 48 hours prior to each experiment.

Drug pharmacokinetic studies were performed via both the intravenous and transvaginal modes of administration. During the first series of experiments, the intravenous route of administration was utilized to determine the initial half-lives of the experimental compound. In the second series of experiments, the intravenous and transvaginal routes of administration were compared in the same rabbit.

For the half-life experiments, after an 18 hour overnight fast, each rabbit was premedicated with ketamine (35 mg/kg, i.m.), xylazine (5 mg/kg, i.m.), and atropine (0.5 mg, i.m.). Each rabbit was intubated and anesthesia was maintained with isoflurane (1–3%). Vital signs were monitored throughout the experiment via a pulse oximeter. Rabbit body temperature was kept constant by a recirculating heating pad. Intravenous access was achieved by placement of a 22 gauge TEFLON catheter in the peripheral ear vein. Intra-arterial access was achieved by placement of a 22 gauge TEFLON catheter in the central artery in the ear. A heat lamp was used to warm the ears to promote peripheral blood flow.

After the rabbit was anesthetized, the mixture containing labeled and unlabeled drug was injected through the ear vein over a 10 second to 2 minute period. Blood samples were drawn through the arterial line at 0.1, 0.25, 0.5, 0.75, 2, 4, 6, 8,10,12 and 24 hours relative to the time of injection. Blood samples (1 mL) were placed in a polypropylene tube containing EDTA. The blood was centrifuged at 2000 rpm for 10 minutes and 0.5 mL of plasma was placed into a scintillation vial.

Solvable tissue solubilizer (0.5 ml) (Packard, Meridian, Conn.) was added to the plasma samples and samples were vortexed for 30 seconds. 10 mL of Hionic-Fluor scintillation cocktail (Packard) was added and samples were vortexed for 1 minute before they were placed on the scintillation counter.

For the transvaginal experiments, vaginal suppositories were formulated and kept on ice. The suppository was introduced into the rabbit vagina using the barrel of a plastic transfer pipette (Baxter, McGaw Park, Ill.) and a tuberculin syringe as the plunger to load the suppository into the vagina to a depth of 7 to 8 cm. Blood samples were taken at 0.1, 0.25, 0.5, 0.75, 2, 4, and 6 hours relative to suppository administration.

0.1 to 0.2 gm uterine muscle biopsies were obtained at 0.2, 0.35, 0.5, 0.75, 2, 4, and 6 hours relative to drug administration from the uterine horn via a transverse laparatomy. For comparison purposes, gracilis muscle biopsies were taken at 1.5 and 6 hours relative to drug administration. Rabbits were euthanized with pentobarbital at the end of this experiment.

1 mL of tissue solubilizer was added to tissue samples which were then placed in a shaking water bath at 50° C. to incubate overnight. 10 mL of scintillation cocktail (Packard) was added and samples were vortexed for 1 minute, blood samples were procured as previously described, then all samples were placed in the scintillation counter.

The rabbit was allowed to recover and a 7-day washout period was carried out prior to the vaginal administration.

Verapamil was administered as in Example 3. As shown in Table 1, blood levels persisted for a prolonged period of time, and the concentrating effect in the uterine muscle averaged up to 3.5 times that in gracilis muscle at several intervals. Table 1 is a summary of mean concentration ratios after intravaginal administration of Verapamil or Indomethicin.

TABLE 1

Mean Concentration (mg/mL) Ratios After Vaginal Administration

| Drug | At 0.5 hours: | At 1.5 hours: | At 6 hours: |
|---|---|---|---|
| Verapamil (n = 5) | | | |
| Blood/Uterus | 0.72 | 0.67 | 1.51 |
| Blood/Leg | 1.52 | 1.58 | 1.75 |
| Uterus/Leg | 2.67 | 3.16 | 1.40 |
| Indomethacin (n = 2) | | | |
| Blood/Uterus | 2.20 | 2.30 | 2.30 |
| Blood/Leg | 10.40 | 9.10 | 10.70 |
| Uterus/Leg | 4.75 | 4.00 | 4.70 |

Indomethacin was administered by the methods as described in hereinabove but with Indomethacin replacing Verapamil. The results (Table 1) demonstrated that the ratio of uterus to gracilis muscle concentration was 4 or 5 showing that after vaginal administration there were much higher concentrations in uterine tissue than in skeletal (gracilis) muscle. The results support the concept of selective and local delivery and uptake.

EXAMPLE 4

Naproxen and Ketorolac Studies

Naproxen sodium salt was obtained from Sigma Chemical Co., St. Louis, Mo. The dose was 1.0 mg/kg body weight. A radiolabel was not added because HPLC was used to determine the amount of Naproxen in plasma and tissue samples. All of the other steps in the preparation of the Naproxen suppository are identical to those of Example 1 with Naproxen replacing Verapamil.

The dose of Ketorolac (Abbott Labs, Chicago, Ill.) was 0.4 mg/kg body weight. $^{14}$C- Ketorolac was obtained from Syntex/Roche, Nutley, N.J. Labeled Ketorolac (10–14 $\mu$Ci) was added to the unlabeled compound. Lactic acid, 5 mg/suppository, was added to buffer the pH of the vagina which changes during the menstrual cycle. All of the other steps in the preparation of the Ketorolac suppository are identical to those of Example 1 with Ketorolac replacing Verapamil.

Naproxen was administered by the methods as described but with Naproxen replacing Verapamil. HPLC was performed on the plasma samples and on the reconstituted extract of homogenized tissue specimens.

Intravenous, oral (PO) dosing, and transvaginal drug delivery were compared.

$^{14}$C-Ketorolac was obtained from Syntex/Roche, Nutley, N.J. Prior to oral administration of intravenous injection, cold Ketorolac (Abbott Labs, Chicago, Ill.) (0.4 mg/kg body weight) was combined with labeled Ketorolac (10–14 $\mu$Ci) and saline to bring volume to 0.5 cc.

The rabbit stomach needs to be empty for oral dosing (PO) experiments but has been shown not empty after a 24 hour fast. For oral dosing, each rabbit was anesthetized, intubated and anesthesia maintained with isoflurane (1–3%) the day prior to surgery. Gastric lavage was used to remove the stomach contents. The rabbit was allowed to recover and was muzzled overnight so that the rabbit would not eat its own feces. 250–300 cc of Lactated Ringers was injected subcutaneously to maintain body fluids overnight.

Labeled/unlabeled Ketorolac was administered 0.4 mg/kg body weight, 10–14 $\mu$Ci, through a long thin tube into the rabbit stomach under isoflurane anesthesia, the tubing then rinsed with 10 cc of warm water before removal. Blood samples were taken at 0.1, 0.25, 0.5, 1, 1.5, 2, 3, 4, 6, 8, 12, 18 and 24 hours relative to suppository administration. Tissue samples were taken at 0.25, 0.5, 1, 1.5, 2, 3, 4, 6, 12, 18 and 24 hours. Each rabbit was allowed to recover after 6 hours and was anesthetized with Propofol, IV, 1.5 mg/kg body weight bolus and maintained by isoflurane by mask for the 12, 18 and 24 hour samples. Rabbits were euthanized with pentobarbital at the end of this experiment. Samples were prepared and counted on the scintillation counter as in Example 3.

Intravenous Ketorolac samples were taken as described in Example 3 for Verapamil except that they were taken at the time points listed for the Ketorolac PO experiments above.

Transvaginal Ketorolac was delivered by suppository as described in Example 3 for Verapamil except that they were taken at the time points listed for the Ketorolac PO experiments above.

The mean calculated values the pharmacological parameters are listed in Table 2. It is noteworthy that the calculated area under the curve for systemic availability and uterine availability following transvaginal administration was between 2 and 3 times greater than those values observed for oral administration. This documents our concept of a specific delivery and accumulation of pharmacologic agents by transvaginal administration that exceeds that of oral administration. These experimental data are referred to in the claims which we make for a unique and specific drug delivery mechanism for treating dysfunction of uterine muscle.

The mechanism on which the current method is based for the higher concentrations of pharmacologic agents observed in uterine muscle after transvaginal administration is that of a specific and unique vascular or lymphatic channel or physiologic mechanism which permits a higher uterine bioavailability for drugs administered transvaginally. These concepts were confirmed with nonsteroidal, anti-inflammatory drugs indomethacin, ketorolac and verapamil. The unique delivery system which is disclosed permits the use of lower concentrations of drug to be administered, lower systemic concentrations to be achieved thereby providing greater localized tissue concentration and fewer side effects. This delivery system can be applied to the numerous classes of drugs.

EXAMPLE 5

Preparation of a Gel Containina Naproxen for Intravaginal Application 250 mL of isotonic saline is heated to 80° C. and 1.50 grams of Methocel are added, with stirring. The resultant mixture is allowed to stand at room temperature for 2 hours. Then 120 mg of Naproxen is mixed together with 10 mg of Tween 80. The Naproxen/Tween mixture and a quantity of isotonic saline sufficient to bring the total volume to 500 mL were added to the gel and thoroughly mixed.

EXAMPLE 6

Preparation of Indomethacin Containing Lotion for Intravaginal Application

Indomethacin (I-7378, Sigma/Aldrich, St. Louis, Mo.) (50 mg) is added to one mL of JERGENS® standard fragrance free lotion.

TABLE 2

IV, Oral, Transvaginal Ketorolac Comparative Pharmacokinetic Data

|  | IV N = 3 | ORAL N = 3 | TRANSVAGINAL N = 4 |
| --- | --- | --- | --- |
| Blood Half-life (h) | 4.77 ± 1.38 | 4.06 ± 0.55 | 4.04 ± 1.93 |
| Uterus Half-life (h) | 5.25 ± 1.28 | 6.11 ± 4.73 | 4.96 ± 1.66 |
| Area under the Curve (µg/ml) h |  |  |  |
| Blood | 41.93 ± 20.59 | 7.48 ± 4.73 | 33.29 ± 19.98 |
| Uterus | 14.95 ± 6.87 | 3.59 ± 1.44 | 10.86 ± 4.21 |
| Calc. Bioavailability (%) |  |  |  |
| Blood | *100 | 13.74 ± 1.76 | 67 ± 26.55 |
| Uterus | *100 | 23.99 ± 9.57 | 62.41 ± 29.36 |

*arbitrarily set at 100 for all other calculations

Results seen in Table 2 are further confirmed by findings shown in FIG. 20. FIG. 20 graphically illustrates the differences in vaginal (FIGS. 20C and D) and blood (FIG. 20A and B) concentration of ketorolac. As seen in FIG. 20, for ketorolac, there is a greater area under the time concentration curve after transvaginal drug delivery than occurring after oral delivery. The calculated uterine bioavailability, based on comparison to the IV route with transvaginal delivery, is more than two times that observed with oral delivery.

These data further substantiate claims for a unique and specific delivery system for treating medical conditions arising from dysfunction in the uterus. By the way of invention, the drugs are specifically delivered to the site of the pathophysiology in doses which produce much lower system concentrations and thereby fewer side effects.

EXAMPLE 7

Preparation of Ibuprofen Containing Gel for Intravapinal Application

Ibuprofen (I-4883, Sigma/Aldrich, St. Louis, Mo.) (200 mg) is added to one mL of gel comprised of the following ingredients: glycerin, mineral oil, polycarbophil, carbomer 934P, hydrogenated palm oil, glyceride, sodium hydroxide, sorbic acid, and purified water.

EXAMPLE 8

Preparation of Vaginal Suppositories

A vaginal suppository is prepared for intravaginal administration of each one of the following drugs at the indicated dose: Aspirin (975 mg), Piroxicam (20 mg), Indomethacin (50 mg), Fenamate (500 mg), Sulindac (200 mg), Nabumetone (750 mg), Ketorolac (10 mg), Ibuprofen (200 mg), Phenylbutazone (50 mg, P-8386, Sigma), Bromfenac (50 mg), Naproxen (550 mg), Lidocaine (100 mg), Mepivacaine (0.2 mg), Etidocaine (200 mg), Bupivacaine (100 mg), 2-Chloroprocaine hydrochloride (100 mg), Procaine (200 mg, P-9879, Sigma), Tetracaine hydrochloride (20 mg, T-7508, Sigma), Diltaizem (60 mg), Israpidine (10 mg), Nimodipine (30 mg), Felodipine (450 mg), Nifedipine (90 mg), Nicardipine (30 mg), Ritodrine (150 mg), Bepridil (300 mg), Dofetilide (1 mg), E-4031 (1 mg), Almokalant (1 mg), Sematilide (1 mg), Ambasilide (1 mg), Azimilide (1 mg), Tedisamil (100 mg), RP58866 (100 mg), Sotalol (240 mg), Ibutilide (1 mg), Terbutaline (5 mg), Salbutamol (1 mg), Piroxicam (20 mg), Metaproterenol sulphate (20 mg), nitroglycerin (3 mg), isosorbide dinitrate (40 mg), isosorbide mononitrate (120 mg), Celecoxib (200 mg), Meloxicam (7.5 mg) and Flosulide (20 mg). All of the steps in the preparation of the drug suppository are identical to those of Example 1 except that no radiolabeled compound is used and the indicated amount of drug is used in place of Verapamil.

The quantity of vaginal dosage form needed to deliver the desired dose will of course depend on the concentration of the active ingredient in the composition. The therapeutic dosage range for vaginal administration of the compositions of the present invention will vary with the size of the patient.

EXAMPLE 9

Preparation of Other Compositions

A composition is prepared for intravaginal administration of each one of the following drugs at the indicated dose: Aspirin (975 mg), Piroxicam (20 mg), Indomethacin (50 mg), Fenamate (500 mg), Sulindac (200 mg), Nabumetone (750 mg), Ketorolac (10 mg), Ibuprofen (200 mg), Phenylbutazone (50 mg, P-8386, Sigma), Bromfenac (50 mg), Naproxen (550 mg), Lidocaine (100 mg), Mepivacaine (0.2 mg), Etidocaine (200 mg), Bupivacaine (100 mg), 2-Chloroprocaine hydrochloride (100 mg), Procaine (200 mg, P-9879, Sigma), Tetracaine hydrochloride (20 mg, T-7508, Sigma), Diltaizem (60 mg), Israpidine (10 mg), Nimodipine (30 mg), Felodipine (450 mg), Nifedipine (90 mg), Verapamil (120 mg), Nicardipine (30 mg), Ritodrine (150 mg), Bepridil (300 mg), Dofetilide (1 mg), E-4031 (1 mg), Almokalant (1 mg), Sematilide (1 mg), Ambasilide (1 mg), Azimilide (1 mg), Tedisamil (100 mg), RP58866 (100 mg), Sotalol (240 mg), Ibutilide (1 mg) Terbutaline (5 mg), Salbutamol (1 mg), Metaproterenol sulphate (20 mg), nitroglycerin (3 mg), isosorbide dinitrate (40 mg), isosorbide mononitrate (120 mg), Celecoxib (200 mg), Meloxicam (7.5mg) and Flosulide (20 mg). Each of the drugs listed in this example are substituted in Example 4, 5, 6 or 7, unless previously described, and repetition of the procedures there detailed affords other compositions according to the invention.

The quantity of vaginal dosage form needed to deliver the desired dose will of course depend on the concentration of the active ingredient in the composition. The therapeutic dosage range for intravaginal administration of the compositions of the present invention will vary with the size of the patient.

While the invention has been described in terms of various preferred embodiments, the skilled artisan will appreciate that various modifications, substitutions, omissions and additions may be made without departing from the spirit thereof. Accordingly, it is intended that the scope of the present invention be limited solely by the scope of the following claims.

EXAMPLE 10

Preparation of Vaginal Medicated Tamping

Preparation of vaginal medicated tampons is essentially as described in Example 8. The drugs listed in Example 8 are added to the tampon materials as powders, solutions, suspension or emulsions either before the tampon is fabricated or the prefabricated tampons are soaked in the solution, suspension, emulsion or other fluid preparation The amount of the drug is such that it assures that the dose administered by vaginal tampon is at least as high as the one indicated in Example 8 and is delivered transvaginally in a dose linear manner, as much as possible.

What is claimed is:

1. A medicated intravaginal device for a transvaginal delivery of a pharmaceutical agent to the uterus of a female subject,
    wherein said device is a vaginal tampon, vaginal tampon-like device, vaginal ring, vaginal pessary or vaginal sponge,
    wherein said device is impregnated with a pharmaceutical composition comprising the pharmaceutical agent;
    wherein said device, when inserted intravaginally, maintains contact with the vaginal epithelium and releases said pharmaceutical agent, and
    wherein the concentration of said pharmaceutical agent released from the medicated device to the vaginal epithelium is sufficient for transvaginal delivery of a therapeutically effective dose of said pharmaceutical agent to the uterus of the female subject.

2. The device of claim 1 wherein the pharmaceutical agent is selected from the group consisting of a nonsteroidal anti-inflammatory drug, anti-prostaglandin, prostaglandin inhibitor, COX-2 inhibitor, local anesthetic, calcium channel blocker, potassium channel blocker, β-adrenergic agonist, leukotriene blocking agent, smooth muscle inhibitor, vasodilator, and a drug capable of inhibiting dyskinetic muscle contraction.

3. The device of claim 2 wherein the device is the tampon or tampon-like device, and wherein said pharmaceutical composition further comprises a pharmaceutically acceptable, non-toxic excipient, a mucoadhesive agent and a penetration enhancer.

4. The device of claim 3, wherein the pharmaceutical agent is the nonsteroidal antiinflammatory drug suitable for prevention or treatment of dysmenorrhea.

5. The device of claim 3 wherein the medicated tampon is configured to make physical contact with the cervix of the uterus.

6. The device of claim 5 wherein said pharmaceutical composition is formulated as a cream, lotion, foam, solution, gel, tablet, bioadhesive microparticle or a vaginal suppository for release from the medicated device and for transvaginal delivery into uterus.

7. A medicated device for delivering a pharmaceutical agent to the uterus of a human female subject, said device comprising
    a) a tampon or tampon-like device;
    b) a porous cup affixed to the tampon or tampon-like device and configured to fit around the cervix of the uterus, and
    c) a non-absorbing axial tube extending through the porous cup into the tampon, the tube having a first opening disposed to receive fluid flow from the uterus, and a second opening disposed to deliver the fluid flow to the tampon.

8. The device of claim 7, wherein the cup is a foam cup comprising a rim for encircling the cervix.

9. The device of claim 8, wherein the rim comprises fingers extending into the fornix area around the cervix.

10. The device of claim 9, wherein the rim comprises a pharmaceutical composition comprising essentially of the pharmaceutical agent selected from the group consisting of a nonsteroidal anti-inflammatory drug, anti-prostaglandin, prostaglandin inhibitor, COX-2 inhibitor, local anesthetic, calcium channel blocker, potassium channel blocker, β-adrenergic agonist, leukotriene blocking agent, smooth muscle inhibitor, vasodilator, and a drug capable of inhibiting dyskinetic muscle contraction.

11. The device of claim 10, wherein the rim is positioned away from the direct flow of fluid from the uterus.

12. The device of claim 7, wherein the porous foam cup comprises a pharmaceutical composition consisting essentially of the pharmaceutical agent selected from the group consisting of a nonsteroidal anti-inflammatory drug, anti-prostaglandin, prostaglandin inhibitor, COX-2 inhibitor, local anesthetic, calcium channel blocker, potassium channel blocker, β-adrenergic agonist, leukotriene blocking agent, smooth muscle inhibitor, vasodilator, and a drug capable of inhibiting dyskinetic muscle contraction.

13. The device of claim 12, further comprising injecting means for injecting the pharmaceutical agent into the porous foam after the device has been inserted in a female vagina.

14. The device of claim 13, wherein the injecting means comprises
 a) a reservoir containing the pharmaceutical agent;
 b) a non-absorbing delivery tube having a first opening connected to the reservoir for receiving the pharmaceutical agent from the reservoir and at least a second opening disposed to deliver pharmaceutical agent to the porous foam cup; and
 c) means for forcing the pharmaceutical agent from the reservoir through the delivery tube into the porous foam.

15. The device of claim 14, wherein the delivery tube comprises a wall having a plurality of perforations disposed to deliver pharmaceutical agent to the porous foam cup.

16. A device for delivering a pharmaceutical agent to a female uterus, the device comprising a tampon or tampon-like device configured to make physical contact with the vaginal epithelium,
 wherein said tampon or tampon-like device is impregnated with a pharmaceutical composition comprising the pharmaceutical agent;
 wherein said device, when inserted intravaginally, maintains contact with the vaginal epithelium and releases said pharmaceutical agent;
 wherein the concentration of said pharmaceutical agent released from said device to the vaginal epithelium is sufficient for transvaginal delivery of a therapeutically effective dose of said pharmaceutical agent to uterus of the female subject; and
 wherein said pharmaceutical agent is selected from the group consisting of a nonsteroidal anti-inflammatory drug, anti-prostaglandin, prostaglandin inhibitor, COX-2 inhibitor, local anesthetic, calcium channel blocker, potassium channel blocker, β-adrenergic agonist, leukotriene blocking agent, smooth muscle inhibitor, vasodilator and a drug capable of inhibiting dyskinetic muscle contraction.

17. The device of claim 16, wherein the device is the tampon comprising absorbent fibers containing the pharmaceutical agent, which fibers, in use, make contact with the cervix.

18. The device of claim 17, wherein said device is impregnated with the pharmaceutical composition comprising said pharmaceutical agent and wherein said composition is formulated as a cream, lotion, foam, solution, gel, tablet, bioadhesive microparticle or vaginal suppository.

19. The device of claim 18, wherein the pharmaceutical agent is the nonsteroidal antiinflammatory drug.

20. The device of claim 19, wherein the nonsteroidal antiinflammatory is ketorolac, naproxen or ibuprofen suitable for prevention and treatment of dysmenorrhea.

21. A device for delivering a pharmaceutical agent to a female uterus, the device comprising
 a) absorbing means for absorbing fluid discharged from the uterus;
 b) delivering means for delivering the pharmaceutical agent; and
 c) conveying means for preferentially conveying fluid discharged from the uterus to the absorbing means and thereby preventing contact of the fluid with the pharmaceutical agent.

22. The device of claim 21, wherein
 the absorbing means comprises a tampon, tampon-like device, ring, pessary or sponge,
 wherein the delivering means comprises a suppository, foam, paste and gel annularly disposed about the device and configured to deliver the pharmaceutical agent to the epithelium of the vagina or a porous foam cup affixed to the tampon and configured to fit around the cervix of the uterus, the porous foam containing the pharmaceutical agent, and
 wherein the conveying means comprises a non-absorbing axial tube extending into the tampon, the tube having a first opening disposed to receive fluid flow from the uterus, and a second opening disposed to deliver the fluid flow to the tampon.

* * * * *